United States Patent
Vargas et al.

(10) Patent No.: US 9,730,743 B2
(45) Date of Patent: Aug. 15, 2017

(54) TROCHANTER ATTACHMENT DEVICE

(71) Applicant: Zimmer, Inc., Warsaw, IN (US)

(72) Inventors: Joseph R. Vargas, Garnerville, NY (US); Timothy A. Hoeman, Morris Plains, NJ (US); Jorge Montoya, Madison, NJ (US); Louis Kwong, Glendale, CA (US); Ray Zubok, Midland Park, NJ (US); Keith A. Roby, Jersey City, NJ (US); Jeff Dickerson, Warsaw, IN (US); Anthony Lusardi, Blairstown, NJ (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 14/720,339

(22) Filed: May 22, 2015

(65) Prior Publication Data

US 2015/0250508 A1    Sep. 10, 2015

Related U.S. Application Data

(63) Continuation of application No. 13/970,073, filed on Aug. 19, 2013, now Pat. No. 9,050,150.
(Continued)

(51) Int. Cl.
*A61F 2/32* (2006.01)
*A61B 17/80* (2006.01)
(Continued)

(52) U.S. Cl.
CPC ............ *A61B 17/808* (2013.01); *A61B 17/74* (2013.01); *A61F 2/30739* (2013.01); *A61F 2/32* (2013.01);
(Continued)

(58) Field of Classification Search
None
See application file for complete search history.

(56) References Cited

U.S. PATENT DOCUMENTS

| 4,227,518 A | 10/1980 | Aginsky |
| 5,282,861 A | 2/1994 | Kaplan |
(Continued)

FOREIGN PATENT DOCUMENTS

| DE | 4320086 A1 | 12/1994 |
| DE | 19517275 A1 | 11/1996 |
(Continued)

OTHER PUBLICATIONS

"European Application Serial No. 13753767.6, Communication mailed Apr. 30, 2015", 2 pgs.
(Continued)

*Primary Examiner* — Sameh Boles
(74) *Attorney, Agent, or Firm* — Schwegman Lundberg & Woessner, P.A.

(57) ABSTRACT

A trochanter attachment device can include a plate for attachment to an inner portion of a greater trochanter of a femur, a collar for attaching the plate to a hip implant, and a fastener for securing the collar to a hip implant. The trochanter attachment device can include a groove or other feature for receiving a reinforcing material, such as a wire or a cable, such as to reinforce an attachment of the device to the greater trochanter and/or the hip implant. The trochanter attachment device can include an insert attachable to the plate and configured to attach the plate to the greater trochanter. All or a portion of the plate and/or the insert can include a porous material, such as to promote bone ingrowth of the greater trochanter.

18 Claims, 10 Drawing Sheets

Related U.S. Application Data

(60) Provisional application No. 61/684,898, filed on Aug. 20, 2012.

(51) Int. Cl.
*A61B 17/74* (2006.01)
*A61F 2/30* (2006.01)

(52) U.S. Cl.
CPC . *A61F 2240/001* (2013.01); *A61F 2250/0058* (2013.01)

(56) References Cited

U.S. PATENT DOCUMENTS

| | | | |
|---|---|---|---|
| 5,356,410 A * | 10/1994 | Pennig | 606/62 |
| 5,462,547 A | 10/1995 | Weigum | |
| 5,658,349 A | 8/1997 | Brooks et al. | |
| 5,665,088 A | 9/1997 | Gil et al. | |
| 6,338,734 B1 | 1/2002 | Burke et al. | |
| 6,379,390 B1 | 4/2002 | Advani et al. | |
| 6,695,884 B1 | 2/2004 | Townley | |
| 7,044,976 B2 | 5/2006 | Meswania | |
| 7,207,993 B1 | 4/2007 | Baldwin et al. | |
| 7,476,255 B2 | 1/2009 | Lester et al. | |
| 7,491,242 B2 * | 2/2009 | Pichon | A61F 2/30734 623/23.21 |
| 7,611,513 B2 | 11/2009 | Deloge et al. | |
| 7,641,698 B1 | 1/2010 | Gibbs et al. | |
| 7,662,189 B2 | 2/2010 | Meswania | |
| 7,828,805 B2 | 11/2010 | Hoag et al. | |
| 7,842,096 B2 | 11/2010 | Fridshtand et al. | |
| 8,021,432 B2 | 9/2011 | Meridew et al. | |
| 8,021,433 B2 | 9/2011 | Meswania et al. | |
| 8,066,779 B2 | 11/2011 | Gibbs et al. | |
| 8,118,868 B2 | 2/2012 | May et al. | |
| 8,979,940 B2 * | 3/2015 | Porter | A61F 2/30739 623/23.15 |
| 9,050,150 B2 | 6/2015 | Vargas et al. | |
| 2007/0129809 A1 * | 6/2007 | Meridew | A61F 2/30724 623/22.32 |
| 2008/0281428 A1 | 11/2008 | Meyers et al. | |
| 2009/0164026 A1 | 6/2009 | Mikami et al. | |
| 2011/0218641 A1 * | 9/2011 | Smith | A61F 2/32 623/22.42 |
| 2011/0233263 A1 | 9/2011 | Hippensteel et al. | |
| 2012/0010720 A1 * | 1/2012 | Dickerson | A61F 2/30734 623/22.42 |
| 2014/0052192 A1 | 2/2014 | Vargas et al. | |
| 2014/0067081 A1 | 3/2014 | Stone | |

FOREIGN PATENT DOCUMENTS

| | | |
|---|---|---|
| EP | 2884947 B1 | 9/2016 |
| FR | 2732891 A1 | 10/1996 |
| WO | WO-2014031535 A1 | 2/2014 |

OTHER PUBLICATIONS

"European Application Serial No. 13753767.6, Response filed Nov. 9, 2015 to Communication mailed Apr. 30, 2015", 11 pgs.

"International Application Serial No. PCT/US2013/055574, International Preliminary Report on Patentability mailed Mar. 5, 2015", 10 pgs.

"U.S. Appl. No. 13/970,073, Notice of Allowance dated Feb. 10, 2015", 10 pgs.

"U.S. Appl. No. 13/970,073, Response filed Jan. 26, 2015 to Restriction Requirement dated Nov. 24, 2014", 7 pgs.

"U.S. Appl. No. 13/970,073, Restriction Requirement dated Nov. 24, 2014", 8 pgs.

"International Application Serial No. PCT/US2013/055574, International Search Report dated Oct. 2, 2013", 6 pgs.

"International Application Serial No. PCT/US2013/055574, Written Opinion dated Oct. 2, 2013", 8 pgs.

"Zimmer Product Brochure "Cable-Ready Cable Grip System" Greater Trochanteric Reattachment Device", 97-2232-013-00 Rev. 2, 2ML, Zimmer, Inc., (2006, 2008, 2009), 4 pgs.

* cited by examiner

US 9,730,743 B2

TROCHANTER ATTACHMENT DEVICE

CLAIM OF PRIORITY

This application is a continuation of U.S. patent application Ser. No. 13/970,073, filed on Aug. 19, 2013, which application claims the benefit of priority of U.S. Provisional Application Ser. No. 61/684,898, filed on Aug. 20, 2012, which applications are incorporated by reference herein in their entirety.

TECHNICAL FIELD

The present patent application relates to orthopedic implants, and more particularly, to an apparatus and method for reattaching the greater trochanter to the femur during or following hip arthroplasty.

BACKGROUND

Orthopedic procedures may be used for the replacement of all, or a portion of, a patient's joint. Total hip arthroplasty may be used to restore function to a diseased or injured hip joint. The hip joint is a ball and socket joint that includes the acetabulum and the femoral head of the femur (or femoral bone). The femur also includes the greater trochanter.

As part of the original hip arthroplasty or a later hip revision surgery, all or a portion of the greater trochanter may become detached from the femur. Existing techniques for reattaching the greater trochanter to the femur can include attaching a metal plate to an outer portion (a lateral side) of the greater trochanter such that the metal plate extends lengthwise down the outer side of the femur. This type of plate may be used with wires or cables that wrap around the greater trochanter and the femur.

OVERVIEW

The present inventors have recognized, among other things, that there is an opportunity for a trochanter attachment device that can provide greater stability to the greater trochanter, such as relative to the femur and a femoral component of a hip implant. More particularly, the present inventors have recognized that a device can be secured to an inner portion (a medial side) of the greater trochanter, as well as to the hip implant, such as to help provide stability to the greater trochanter. The trochanter attachment device described herein can be used, for example, in cases where the greater trochanter is deficient (for example, having cracks and/or missing portions) and/or partially or wholly detached from the femur.

To better illustrate the trochanter attachment device and methods disclosed herein, a non-limiting list of examples is provided here:

In Example 1, a trochanter attachment device comprises a plate, a collar, and a fastener. The plate can have an inner surface and an outer surface configured to attach to an inner portion of a greater trochanter of a femur. The collar can be attached to the inner surface of the plate and configured to connect the plate to a hip implant. The fastener can be configured for securing the collar to the hip implant. A bottom end of the collar can be configured to contact a top surface of the hip implant. An upper portion of the plate can be configured to extend above the top surface of the hip implant when the collar is secured to the hip implant, and a lower portion of the plate can be configured to extend below the top surface of the hip implant when the collar is secured to the hip implant.

In Example 2, the trochanter attachment device of Example 1 is optionally configured such that the fastener includes a screw and a nut configured to engage with the screw and a stem of the hip implant.

In Example 3, the trochanter attachment device of Example 2 is optionally configured such that the nut includes a first end portion having a threaded portion configured to engage with the screw and a second end portion having a threaded portion configured to engage with the stem of the hip implant.

In Example 4, the trochanter attachment device of any one of Examples 2 or 3 is optionally configured such that the nut comprises a spline on an outer surface of the nut. The spline can be configured to engage with an inside surface of the collar.

In Example 5, the trochanter attachment device of Example 2 is optionally configured such that the nut includes a first end portion configured to engage with the screw and a second end portion configured to engage with the stem of the hip implant. The first end portion can include a cone-shaped portion configured to engage with an inside surface of the collar.

In Example 6, the trochanter attachment device of any one of Examples 1-5 optionally further includes an insert configured to be attachable to the outer surface of the plate and configured to attach the plate to the greater trochanter.

In Example 7, the trochanter attachment device of Example 6 is optionally configured such that the insert includes a porous portion.

In Example 8, the trochanter attachment device of Example 7 is optionally configured such that the porous portion includes tantalum.

In Example 9, the trochanter attachment device of any one of Examples 1-8 optionally further includes a ring including a groove extending at least partially circumferentially around an outer surface of the ring. The ring can be configured to be attachable to an outer surface of the collar.

In Example 10, the trochanter attachment device of any one of Examples 1-9 is optionally configured such that the collar includes a groove on an outer surface of the collar configured for receiving a reinforcing material.

In Example 11, the trochanter attachment device of any one of Examples 1-10 is optionally configured such that the fastener includes a screw. The screw can include a groove extending at least partially circumferentially around an outer surface of the screw.

In Example 12, the trochanter attachment device of any one of Examples 1-11 is optionally configured such that the plate and the collar include at least one of stainless steel, cobalt, cobalt-chromium, titanium, tantalum, or one or more alloys thereof.

In Example 13, the trochanter attachment device of any one of Examples 1-12 is optionally configured such that the plate and the collar include a porous tantalum region.

In Example 14, the trochanter attachment device of any one of Examples 1-14 is optionally configured such that the fastener secures the bottom end of the collar to a top surface of a femoral component of the hip implant.

In Example 15, a trochanter attachment device comprises a plate configured to attach to an inner portion of a greater trochanter of a femur, a collar attached to the plate and configured to contact an outer surface of a hip implant to secure the plate to the hip implant, a screw configured to extend through the collar for securing the collar to the hip implant, and a nut having a first end portion and a second end portion. The first end portion of the nut can be configured to engage with the collar and the screw. The second end portion of the nut can be configured to engage with a stem portion of the hip implant. The plate can include at least one aperture configured for receiving a fastener configured to secure the plate to the greater trochanter.

In Example 16, the trochanter attachment device of Example 15 optionally further includes an insert configured to be attachable to an outer surface of the plate and configured to attach the plate to the greater trochanter. The insert can include a porous material.

In Example 17, the trochanter attachment device of Example 16 is optionally configured such that the porous material includes tantalum.

In Example 18, the trochanter attachment device of any one of Examples 15-17 is optionally configured such that the plate and the collar include at least one of stainless steel, cobalt, cobalt-chromium, titanium, tantalum, one or more alloys thereof, or one or more combinations thereof.

In Example 19, the trochanter attachment device of any one of Examples 15-18 is optionally configured such that the outer surface of the plate is configured to attach to an inside portion of the greater trochanter.

In Example 20, a method of securing a greater trochanter to a femur using an attachment device comprising a plate and a collar includes attaching an outer surface of the plate to an inner portion of the greater trochanter. The method further includes attaching the collar to a top surface of a hip implant implantable into the femur and securing the attachment device to at least one of the greater trochanter and the hip implant. The attachment device can be configured such that, when the collar is attached to the top surface of the hip implant, an upper portion of the plate extends above the top surface of the hip implant and a lower portion of the plate extends below the top surface of the hip implant.

In Example 21, the method of Example 20 is optionally configured such that securing the attachment device to at least one of the greater trochanter and the hip implant includes using at least one reinforcing material.

In Example 22, the method of Example 21 is optionally configured such that the at least one reinforcing material includes at least one of a cable, a wire, a bolt, a suture, or one or more combinations thereof, and the attachment device includes at least one feature configured to receive the at least one reinforcing material.

In Example 23, the method of any one of Examples 20-22 is optionally configured such that attaching the outer surface of the plate to an inner portion of the greater trochanter includes placing an insert between the plate and the inner surface of the greater trochanter. The insert can include a porous material.

In Example 24, the device or method of any one or any combination of Examples 1-23 is optionally configured such that all elements or options recited are available to use or select from.

These and other examples and features of the present trochanter attachment devices and methods will be set forth in part in the following Detailed Description. This overview is intended to provide a summary of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
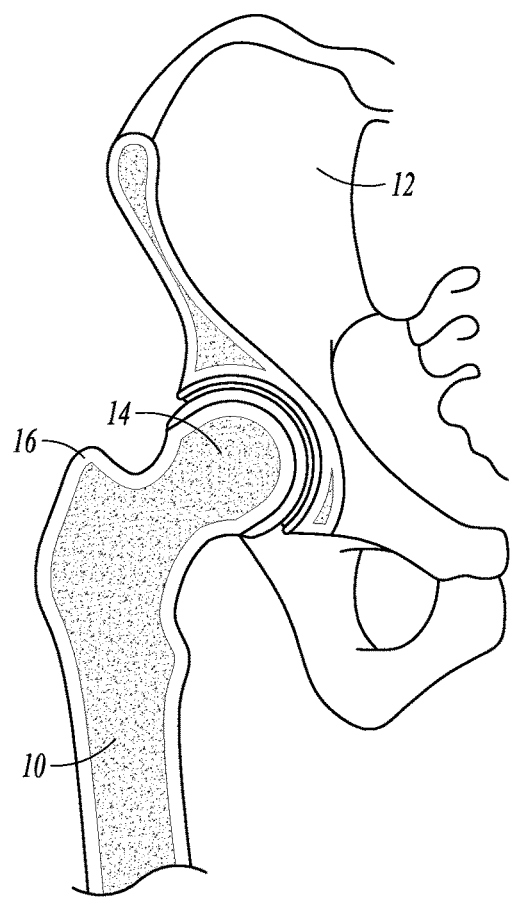
FIG. 1 is a perspective view of a pelvic bone and femur, the femur including a greater trochanter and a femoral head.

The present application relates to devices and methods for attaching or reattaching a greater trochanter of the femur to the femur, such as during a hip arthroplasty and/or as part of a later hip revision surgery. FIG. 1 shows a femur or femoral bone 10 and a pelvic bone 12. As shown in FIG. 1, the femoral bone 10 has different bone regions, including a femoral head 14 and a greater trochanter 16. In hip arthroplasty, at least part of the hip joint is replaced with an implant, such as a prosthesis 50 shown in FIG. 2. The hip prosthesis or implant 50 can include an acetabular shell 52, a femoral head 54, an implant body 56, and a stem 58. In some designs of the prosthesis or implant 50, the implant body 56 can be attached to the stem 58, such as using a nut and threads, taper or other means to engage and connect the implant body 56 to the stem 58.

As part of the hip replacement surgery or arthroplasty, the femoral head 14 can be removed from the femoral bone 10. An opening can be created through the diaphysis of the femoral bone 10. Such an opening can follow the intramedullary canal of the femur and can be configured for receiving the stem 58 of the implant 50. In some cases, the greater trochanter 16 remains intact on the femoral bone 10; however, in some instances, the greater trochanter 16 can become deficient, or partially or completely detached from the femoral bone 10. Even if the greater trochanter 16 remains intact following the original replacement surgery, if a revision has to be performed, the greater trochanter 16 may likely become further compromised or detached as a result of the revision surgery.

Figure 3:
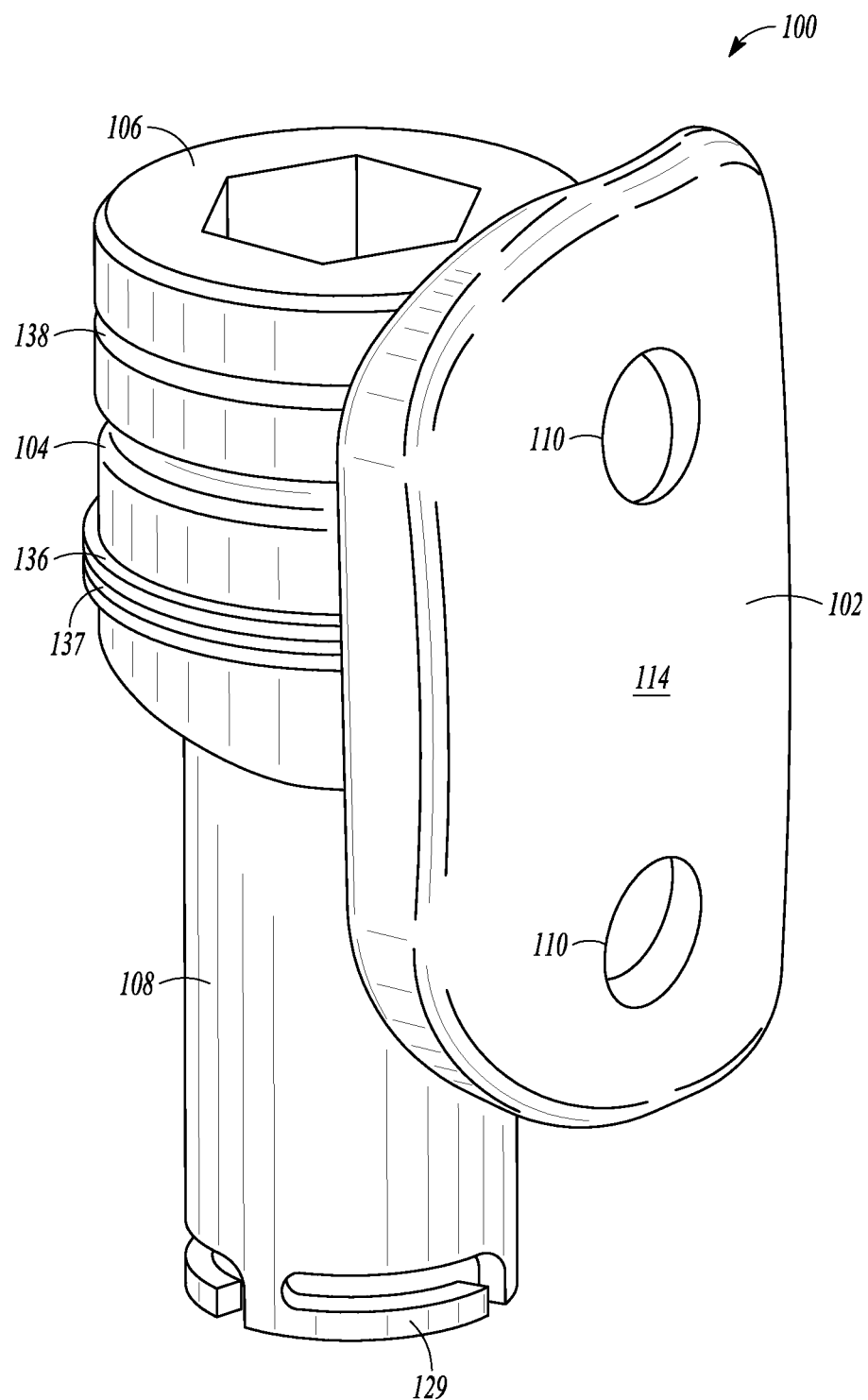
FIG. 3 is a perspective view of an example of a trochanter attachment device in accordance with the present patent application.
Figure 4:
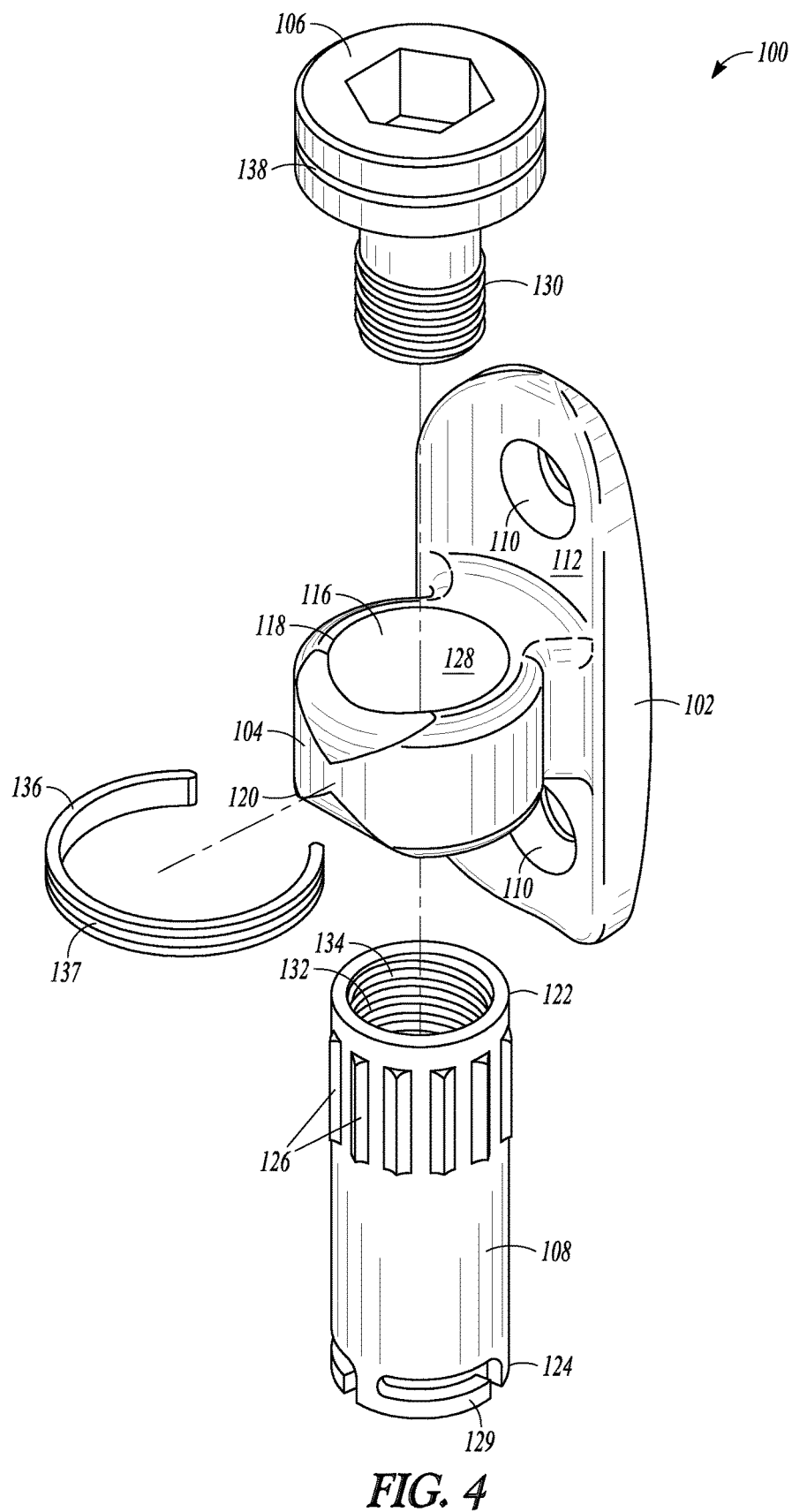
FIG. 4 is an exploded perspective view of the trochanter attachment device of FIG. 3.

FIG. 3 shows an example of a trochanter attachment device 100 that can include a plate 102, a collar 104, a screw 106, and a nut 108. Each of these components is also shown in FIG. 4, which is an exploded view of the trochanter attachment device 100 of FIG. 3. The trochanter attachment device 100 can be used during a hip replacement surgery or during a revision surgery. The plate 102 is configured for attachment to an inner surface or inner portion of the greater trochanter 16. In an example of the attachment device 100 shown in FIGS. 3 and 4, the plate 102 can include one or more apertures 110, which can extend from an inner surface 112 of the plate 102 to an outer surface 114 of the plate 102, and which can be configured to respectively receive a fastener, such as for securing the plate 102 to the greater trochanter 16. Known types of fasteners or fixation devices, such as, for example, bone screws, can be used with the apertures 110. The plate 102 can include more or less apertures 110 compared to the two apertures 110 shown in FIGS. 3 and 4.

Figure 5:
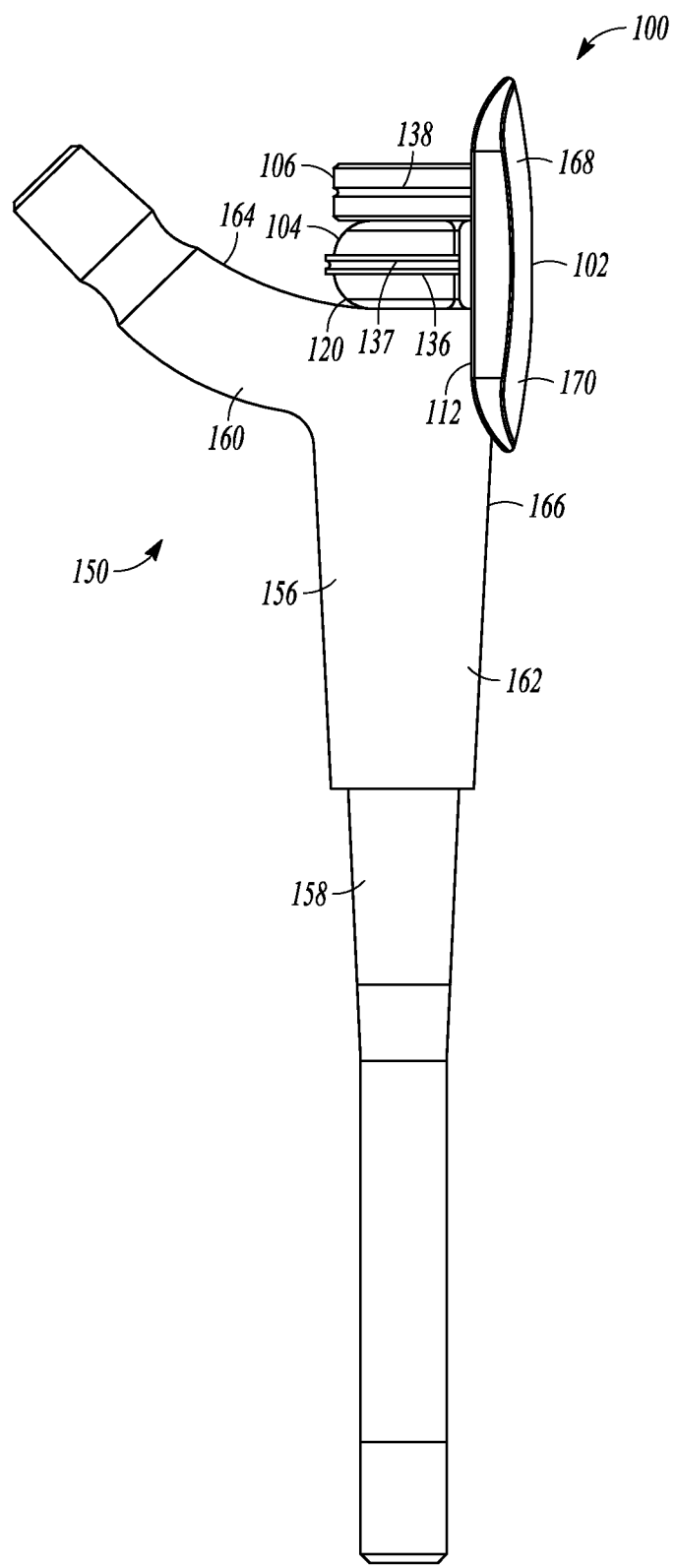
FIG. 5 is a perspective view of the trochanter attachment device of FIG. 3 attached to a proximal femoral component of a hip prosthesis.

The collar 104 can be attached to the plate 102. The collar 104 can be configured to connect the plate 102 to a hip implant, such as shown in FIG. 5. The collar 104 can include an opening 116, which can extend from a first end 118 to a second end 120 of the collar 104. The opening 116 can be configured to engage with the screw 106 and the nut 108. As shown in FIG. 4, the nut 108 can include one or preferably a plurality of splines 126, such as near a first end 122 of the nut 108. In an example, the first end 118 of the collar 104 can be configured to align with the first end 122 of the nut 108, such as to permit the one or more splines 126 to contact an inner surface 128 of the collar 104. In an example, the collar 104, including the inner surface 128, can include or can be formed of a porous structure, such as to permit the splines 126 to grip the porous material on the inner surface 128. As an alternative to or in addition to the porous material, the inner surface 128 can include grooves that engage with the splines 126.

As described further below, a second end 124 of the nut 108 can be configured to engage with a stem of a hip prosthesis or implant. In an example, the nut 108 can include at least one cut-out or recessed track feature 129 at or near the second end 124, such as can be used to secure or lock the nut 108 on the stem of the prosthesis. In the example shown in FIGS. 3 and 4, the nut 108 includes three features 129 on the second end 124. The features 129 can receive or otherwise interact with corresponding respective protruding features on the stem, such as to secure or lock the nut 108 on the stem of the prosthesis.

The screw 106 can be configured to secure the collar 104 to a proximal femoral component of a hip prosthesis, such as shown in FIG. 5, and can include external threads 130 that can engage with corresponding internal threads 132 on an inner surface 134 of the nut 108. The screw 106 can have internal threading and the nut 108 can have external threading. The attachment device 100 can optionally include a ring 136, such as having a groove 137, which can be sized, shaped or otherwise configured to attach to the collar 104, for example, by a snap-fit, bonding, or other attachment technique. The ring 136 can attach to the collar 104 such that the ring 136 can extend circumferentially around at least a portion of the collar 104. As shown in FIGS. 3 and 4, the screw 106 can include a groove 138, such as extending partly or completely around a circumference of the screw 106. The grooves 137 and 138 can be used to receive a wire or cable, such as discussed below. In an example in which the trochanter attachment device does not include a ring, the collar can include an at least partially circumferential groove, and such groove can be used to receive a wire, cable, or other reinforcing material.

In an example of the attachment device 100 shown in FIGS. 3 and 4, the plate 102 and the collar 104 can together be a singular piece and formed of the same material. Otherwise, the plate 102 and the collar 104 can be separate pieces, such as can be bonded together, or attached by another technique; in that case, the plate 102 and the collar 104 can be formed from the same material or of different materials.

In an example, the plate 102 and/or the collar 104 can include or can be formed of a porous structure, such as to facilitate bone ingrowth or regrowth. A porous biomaterial can be useful as a bone substitute, and can have a porosity as low as 55%, 65%, or 75%, or as high as 80%, 85%, or 90%, or within any range defined by any of the foregoing values. In an example, the porous structure can include or can be formed of a material produced using Trabecular Metal™ technology, generally available from Zimmer, Inc. of Warsaw, Ind. Trabecular Metal™ is a trademark of Zimmer, Inc. Such a material can be formed using a foamed polymer (such as polyurethane, as one example) that can be reduced to a reticulated vitreous carbon foam substrate or skeleton. The carbon skeleton can be infiltrated and coated with a first layer of biocompatible metal, such as tantalum, to produce a low density material, and then plated with a second layer of tantalum to produce a high density material. The metal can be deposited on the carbon substrate by a chemical vapor deposition (CVD) process, such as in the manner disclosed in detail in U.S. Pat. No. 5,282,861, the disclosure of which is incorporated herein by reference. One or more other metals, e.g., in addition to tantalum, including alloys thereof, can be used, such as, for example, niobium.

Generally, the porous structure can include a large plurality of ligaments defining open spaces there between, with each ligament generally including a carbon core covered by a thin film of metal, such as tantalum, for example. The open spaces between the ligaments can form a matrix of continuous channels, such as having no dead ends, such as to permit uninhibited growth of cancellous bone through the porous tantalum structure. The porous structure can include up to 75%-85% or more void space therein. In an example, a porous tantalum structure can provide a lightweight, strong porous structure that can be substantially uniform and consistent in composition, and that can closely resemble the structure of natural cancellous bone, which can thereby provide a matrix into which cancellous bone can grow. The porous tantalum structure can be made in a density selected from a variety of densities, such as to selectively tailor the structure for a particular application. The porous tantalum can be fabricated to permit selecting virtually any desired porosity and pore size, and can thus be matched with the surrounding natural bone, such as to provide an improved matrix for bone ingrowth and mineralization.

The plate 102 or the collar 104 can be formed of other porous or non-porous materials. For example, the plate 102 or the collar 104 can be formed of stainless steel, cobalt, cobalt-chromium, titanium, tantalum, or one or more alloys thereof. As described above, the plate 102 or the collar 104 can be formed of the same or different materials. All or a portion of the outer surface 114 of the plate 102 can be a porous tantalum structure, since the outer surface 114 will contact the greater trochanter, and one or more other parts of the plate 102 can be a non-porous material. The plate 102 can be formed of a non-porous material and all or part of the outer surface 114 of the plate 102 can be coated with a porous structure, such as the porous tantalum structure described above. Use of a porous material on the outer surface 114 of the plate 102 can promote fixation of the plate 102 to the greater trochanter and/or can promote bone ingrowth.

The ring 136 can be made of a different material than the collar 104. The ring 136 can be made of a harder or more resistant material than the collar 104, such as to protect the collar 104 if a reinforcing material is used around the collar 104. In an example, the ring 136 can be titanium or a titanium alloy.

The screw 106 or the nut 108 can be made of one or more materials such as can be used in fasteners for devices implanted inside a human or animal body. These materials can include stainless steel, titanium, cobalt, or one or more alloys thereof. In an example, the screw 106 can be made of titanium. In an example, the nut 108 can be made of stainless steel, titanium, cobalt, or one or more alloys thereof.

Figure 2:
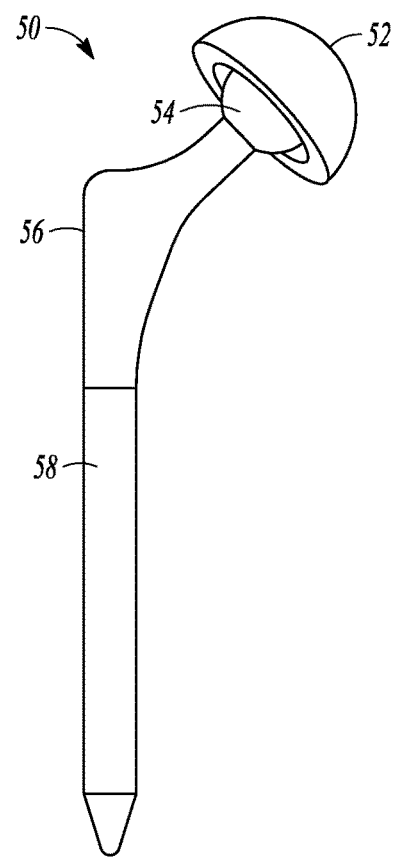
FIG. 2 is a perspective view of a hip prosthesis that may be used in a hip replacement surgery.

FIG. 5 shows an example of the trochanter attachment device 100 of FIGS. 3 and 4 attached to a hip prosthesis or hip implant 150, which can be similar to the prosthesis 50 shown in FIG. 2. As shown in FIG. 5, the trochanter attachment device 100 can attach to a femoral component of the prosthesis or implant 150, which can include a body 156 and a stem 158. The body 156 can include a neck portion 160 and an elongate portion 162. The neck portion 160 can be sized shaped, or otherwise configured to attach to a femoral head that is part of the complete prosthesis implanted in a body.

As shown in FIG. 5, the trochanter attachment device 100 can attach to the neck portion 160 of the body 156. The second end 120 of the collar 104 can contact an outer surface of a top portion 164 of the body 156, which is a top surface of the femoral component of the hip implant 150. The inner surface 112 of the plate 102 can contact an outer surface on a backside 166 of the body 156. The inner surface 112 of the plate 102 may not be centered on the backside 166 of the body 156; rather, the inner surface 112 can be located generally more on one side of the body 156 than the other side. After attachment of the device 100 to the body 156, the plate 102 can have some movement or flexibility relative to the body 156. As shown in FIG. 5, when the collar 104 is attached or secured to the top surface 164 of the hip implant 150, an upper portion 168 of the plate 102 can extend above the top surface 164 and a lower portion 170 of the plate 102 can extend below the top surface 164.

One or more like or different mechanisms can be employed to reinforce attachment of the greater trochanter 16 to the implant 150 and the femur 10, such as once the implant 150 and the attachment device 100 are implanted at least partially into the femur. Examples of possible reinforcement mechanisms can include, but are not limited to, one or more of a cable, a wire, a tiedown, a bolt, a suture, another reinforcement mechanism, or one or more combinations thereof. In an example, the attachment device 100 can be sized, shaped, or otherwise configured for receiving one or more wires; for example, a wire(s) can be received in the groove 137 of the ring 136 and/or in the groove 138 on the screw 106. Such wire(s) can be wrapped around the greater trochanter 16 and/or the femur 10.

Figure 6:
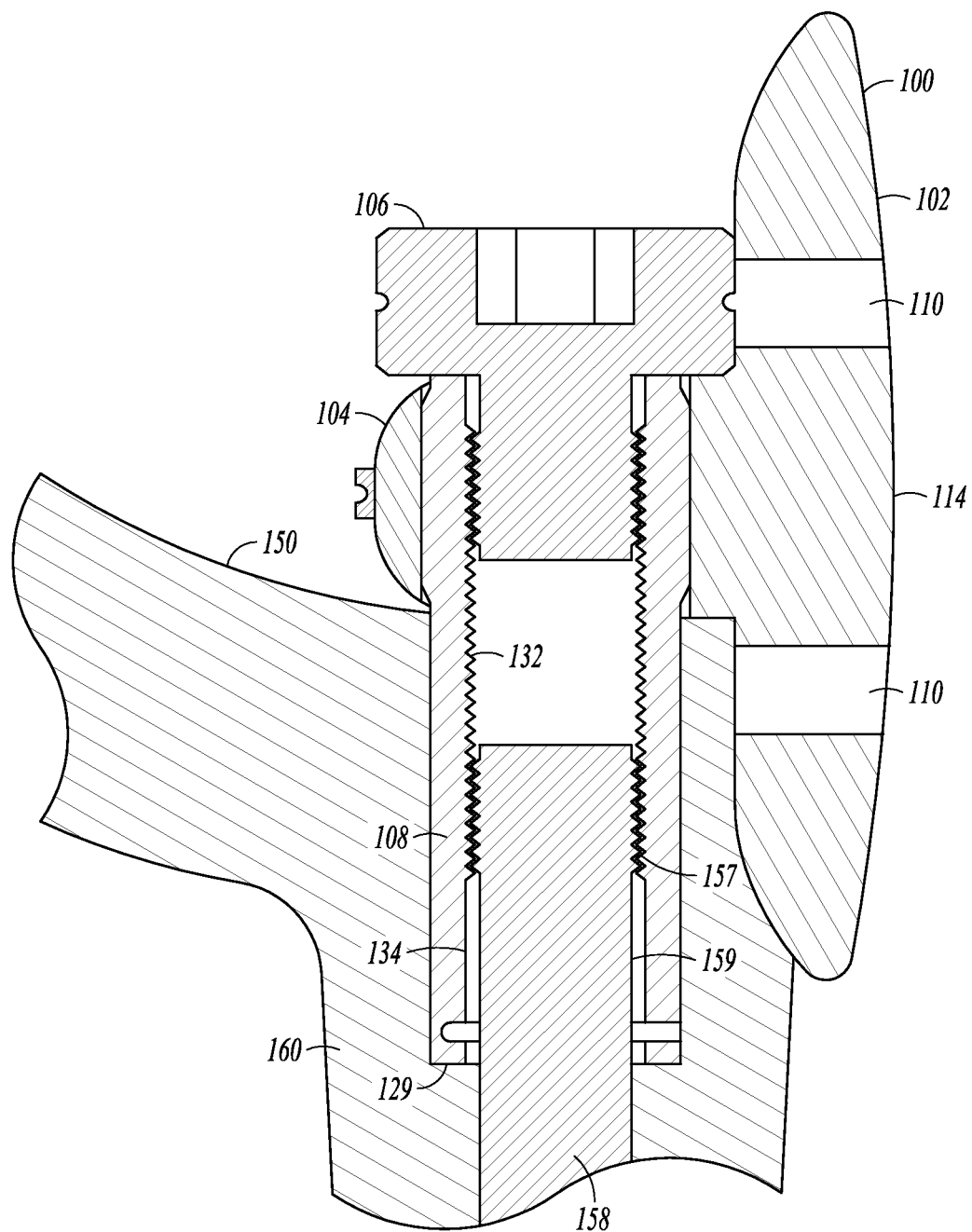
FIG. 6 is a cross-sectional view of the trochanter attachment device and the hip prosthesis of FIG. 5.

FIG. 6 is a cross-section of a portion of FIG. 5, showing an example of the attachment device 100 and the hip prosthesis 150. FIG. 6 shows the nut 108 extending through the neck portion 160 of the prosthesis 150. In an example, the threads 132 on the inner surface 134 of the nut 108 can be configured to engage with corresponding threads 157 on an outer surface 159 of the stem 158 of the prosthesis 150. The nut 108 can be secured on the stem 158, such as using the one or more track features 129, which can be used to lock the nut 108 on the stem 158. The attachment device 100 can be attached to a greater trochanter 16, such as using the one or more apertures 110 on the plate 102, through which a fastener can be inserted, such as to extend through the greater trochanter 16 and the plate 102, at a location on the trochanter 16 aligned with a particular one of the apertures 110.

Some approaches to designs of a proximal femoral component of a hip prosthesis can include a nut that is used to attach a stem to a body portion of the prosthesis. Thus, the attachment device 100 can include or use a nut already used in the prosthesis. The nut from the hip prosthesis can optionally be modified for use in or with the attachment device 100. In an example, such as shown in FIG. 6, a majority of a length of the inner surface 134 of the nut 108 can be threaded. The length of the nut 108 can include more or less threading, as compared to the example shown in FIG. 6, and the specific threading can depend on a design of the screw 106 and/or the stem 158.

In contrast to the prosthesis design shown in FIGS. 5 and 6, hip implants can include a one-piece prosthesis that can include a neck and an elongate body portion. In those designs, an inner surface of the elongate portion 162 can include threads that can be configured to engage with corresponding threads on the nut 108.

As shown in FIGS. 5 and 6, in an example, the outer surface 114 of the plate 102 can have a curved or non-linear shape, such as can be used to promote fitting or fixation of the plate 102 to the greater trochanter 16. In an example, the outer surface 114 of the plate 102 can be generally straight or linear. As part of the preparation for attachment of the trochanter attachment device 100 to a greater trochanter 16, a reamer or other surgical device can be used to shape an inner surface of the greater trochanter 16, such as to accommodate the shape of the plate 102, such as for improved or optimal fitting or fixation of the plate 102 to the greater trochanter 16. In an example, a patient-specific trochanter attachment device 100 can be used, in which case, the outer surface 114 or other feature of a plate 102 of the trochanter attachment device 100 can be shaped to match a particular shape and/or dimension(s) of that particular patient's greater trochanter 16.

Although a screw 106 is shown in the example of the trochanter attachment device 100 shown in FIGS. 3-6, one or more other types of fasteners can be used to secure the collar 104 of the device 100 to an outer surface of the neck portion 160 of the prosthesis 150 and to secure the device 100 to the stem 158 of the prosthesis 150. In an example, the attachment device 100 of FIGS. 3-6 can use a combination of a screw 106 and a nut 108; however, a screw can be used without a nut and the screw can thread directly onto or into a stem of the implant.

Figure 7:
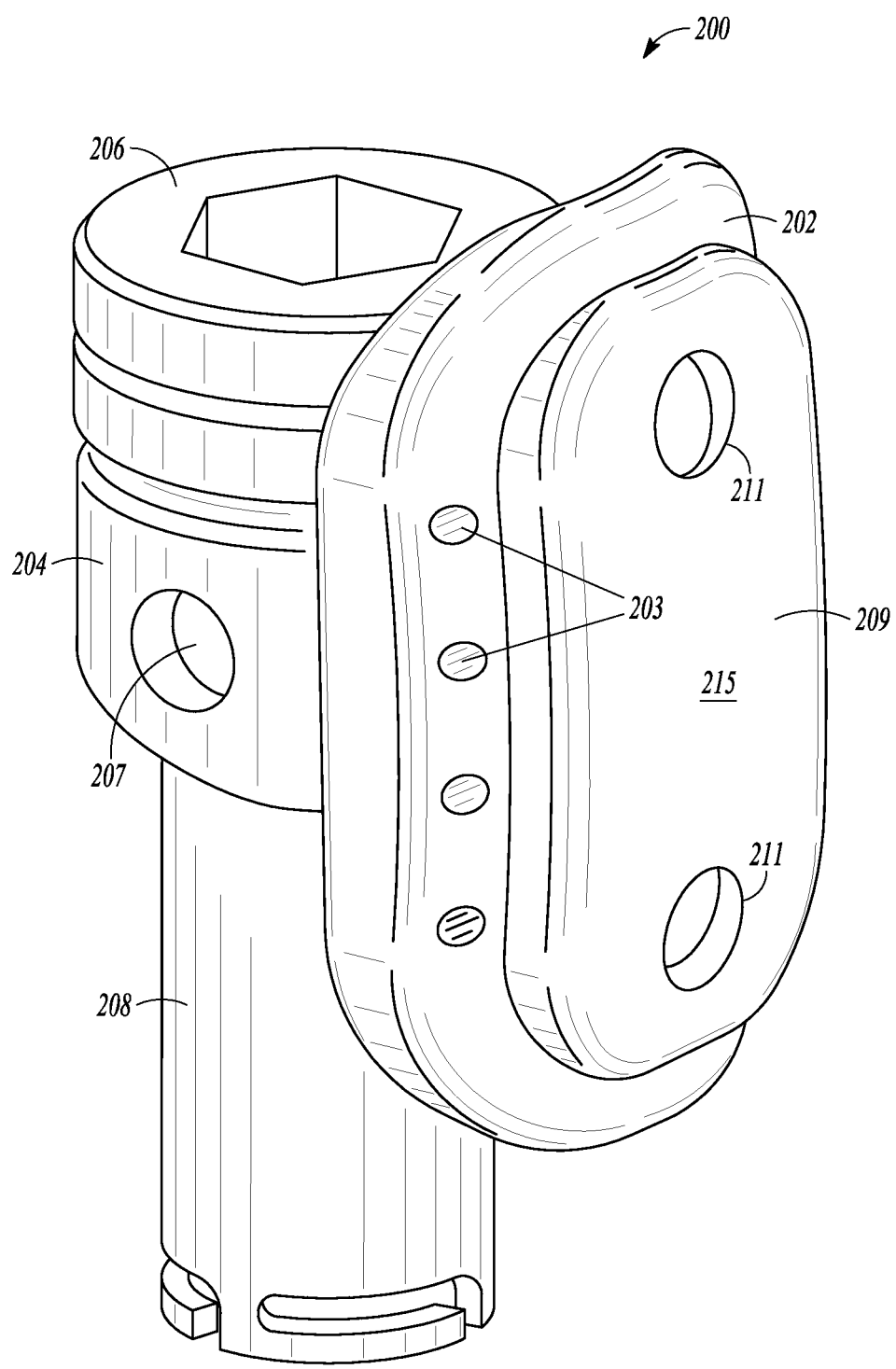
FIG. 7 is a perspective view of an example of a trochanter attachment device in accordance with the present application.

FIG. 7 shows an example of a trochanter attachment device 200, similar to the attachment device 100, and which can include a plate 202, a collar 204, a screw 206, and a nut 208. Each of these components is also shown in FIG. 8, which is an exploded view of the trochanter attachment device 200 of FIG. 7.

Figure 10:
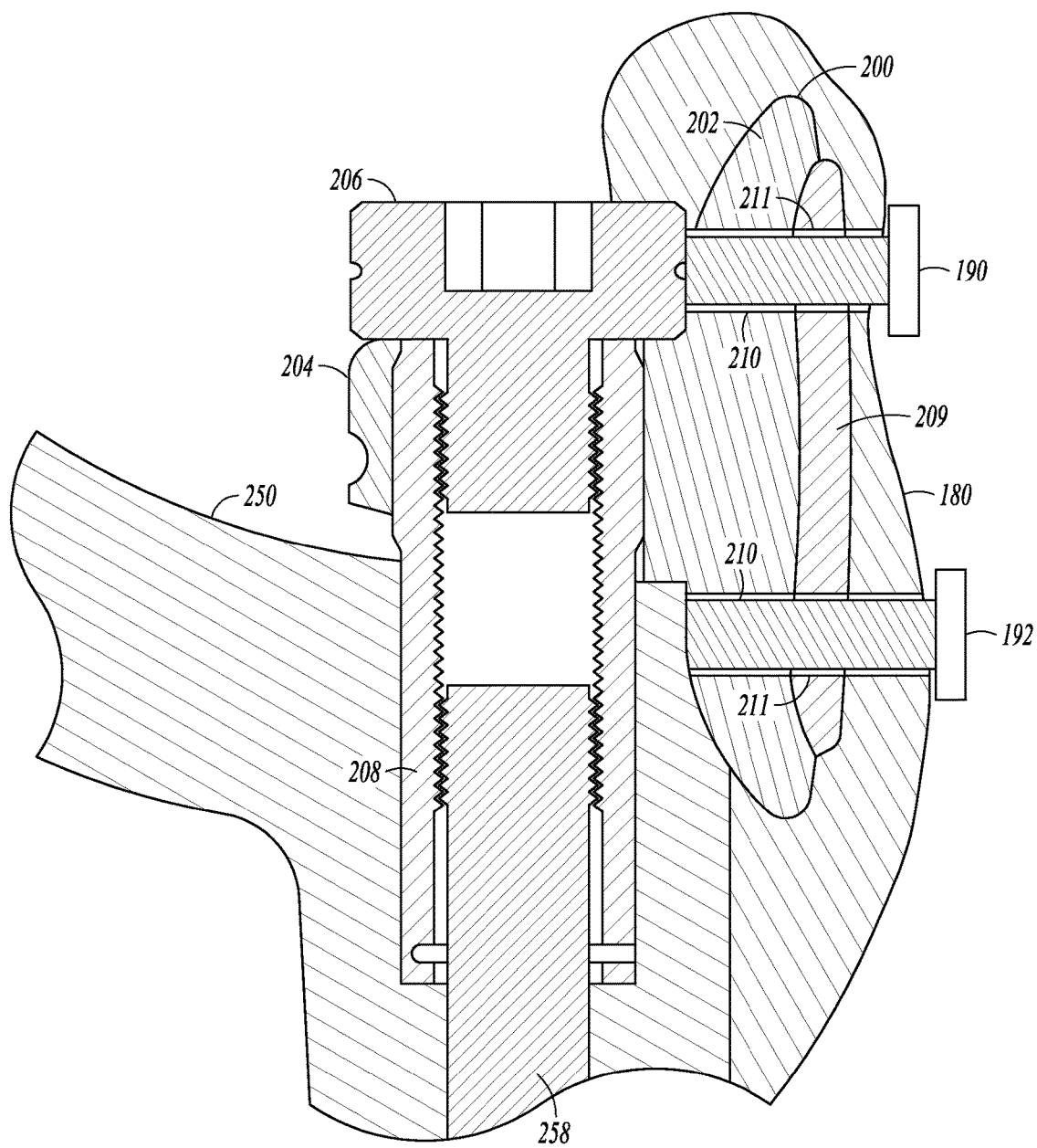
FIG. 10 is a cross-sectional view of the trochanter attachment device, the hip prosthesis and the greater trochanter of FIG. 9.

The attachment device 200 can also include an insert 209, which can be sized, shaped, or otherwise configured to attach to an outer surface 214 of the plate 202. The insert 209 can include one or more apertures 211, such as extending from an inner surface 213 to an outer surface 215 of the insert 209. The apertures 211 on the insert 209 can be arranged or otherwise configured to align with the apertures 210 on the plate 202. As similarly described above for the attachment device 100, the device 200 can be attached to a greater trochanter 16, such as using one or more fasteners and the apertures 210 on the plate 202 and the apertures 211 on the insert 209, an example of which is shown in FIG. 10. The insert 209 can be bonded or otherwise attached to the plate 202, or the insert 209 can be separate from the attachment device 200 before attachment to a greater trochanter 16. The plate 202 and the insert 209 can include more or less than the two apertures shown in FIG. 10 on each of the plate 202 and the insert 209.

The insert 209 can be used for fixation of the plate 202 to the greater trochanter 16 and/or to promote integration of the plate 202 with the bone making up the greater trochanter 16. The insert 209 can include or can be made of a porous material, such as a porous tantalum structure, such as can be made using the Trabecular Metal™ technology described above. The use of a porous material for the insert 209 can help promote ingrowth of the cancellous bone with the insert 209 and/or the plate 202. The insert 209 can be sized, shaped, or otherwise configured such that it matches with a shape of the greater trochanter 16 or a desired portion thereof. In an example, multiple inserts 209, such as of various sizes and shapes, can be made available in a kit or otherwise for use with the trochanter attachment device 200, and the user can select a particular insert 209 to be used, such as based on a particular size and shape of the greater trochanter 16 for a particular patient. In an example, a patient-specific insert 209 can be prepared for a specific patient, prior to surgery, such as based on a predetermined size and shape of the patient's greater trochanter 16, such as can be ascertained using a medical imaging modality or other technique. As an alternative to or in addition to a patient-specific insert 209, a patient-specific plate 202 can similarly be prepared for a patient.

Figure 8:
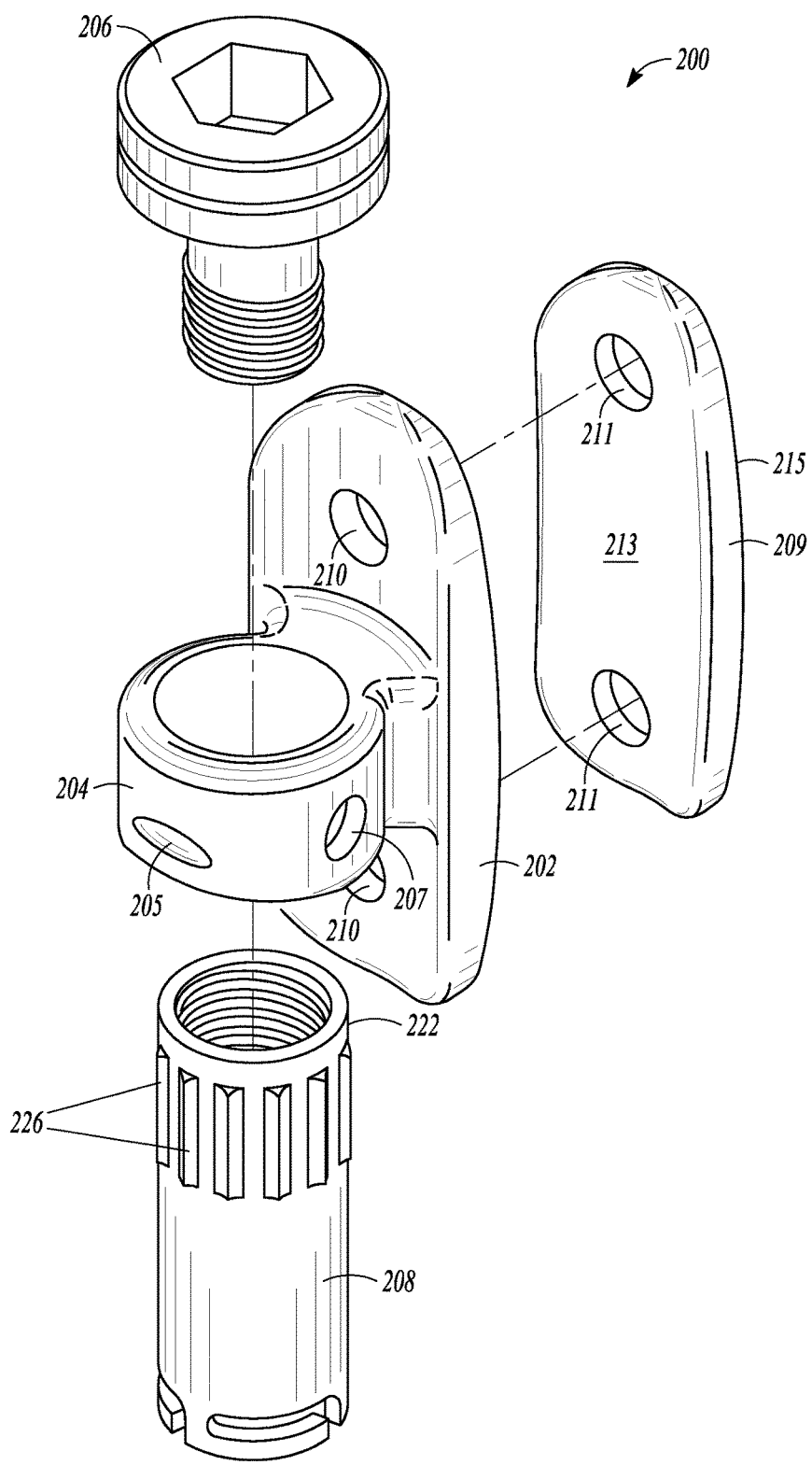
FIG. 8 is an exploded perspective view of the trochanter attachment device of FIG. 7.

As visible in FIG. 8, the collar 204 can include a groove 205, such as can be sized, shaped, or otherwise configured for receiving a wire, cable, or other reinforcing material. The groove 205 can be larger or smaller than that shown in FIG. 8. The collar 204 can include an aperture 207, such as for receiving a screw or other similar or suitable fastener, such as to prevent or limit movement of the screw 206. A similar aperture can be included elsewhere, such as on the other side of the collar 204, which is not visible in FIGS. 7 and 8.

As shown in FIG. 7, the plate 202 can include one or more apertures 203, such as for use as suture wire holes. The apertures 203 can be used to help anchor the greater trochanter 16 to the implant or prosthesis. Similar apertures can be included on the plate 102 of the attachment device 100. The trochanter attachment devices 100 and 200 can include any one or more of a variety of features, in addition to or as an alternative to those described herein, such as for receiving a cable, a wire, or another reinforcing mechanism, such as to reinforce attachment of the device 100 or 200 to the greater trochanter 16 and/or to femoral component of the hip implant.

Similar to a design of the nut 108 of the trochanter attachment device 100, the nut 208 of the trochanter attachment device 200 can include splines 226 near a first end 222 of the nut 208. The splines 226 can be well-suited if an inside portion of the collar 204 is formed of a porous material, such that the splines 226 can grip an inside of the collar 204. In an example, the nut 208 can be configured without any splines. Other known features and methods can be used to attach or fit the nut 208 to the collar 204.

Figure 9:
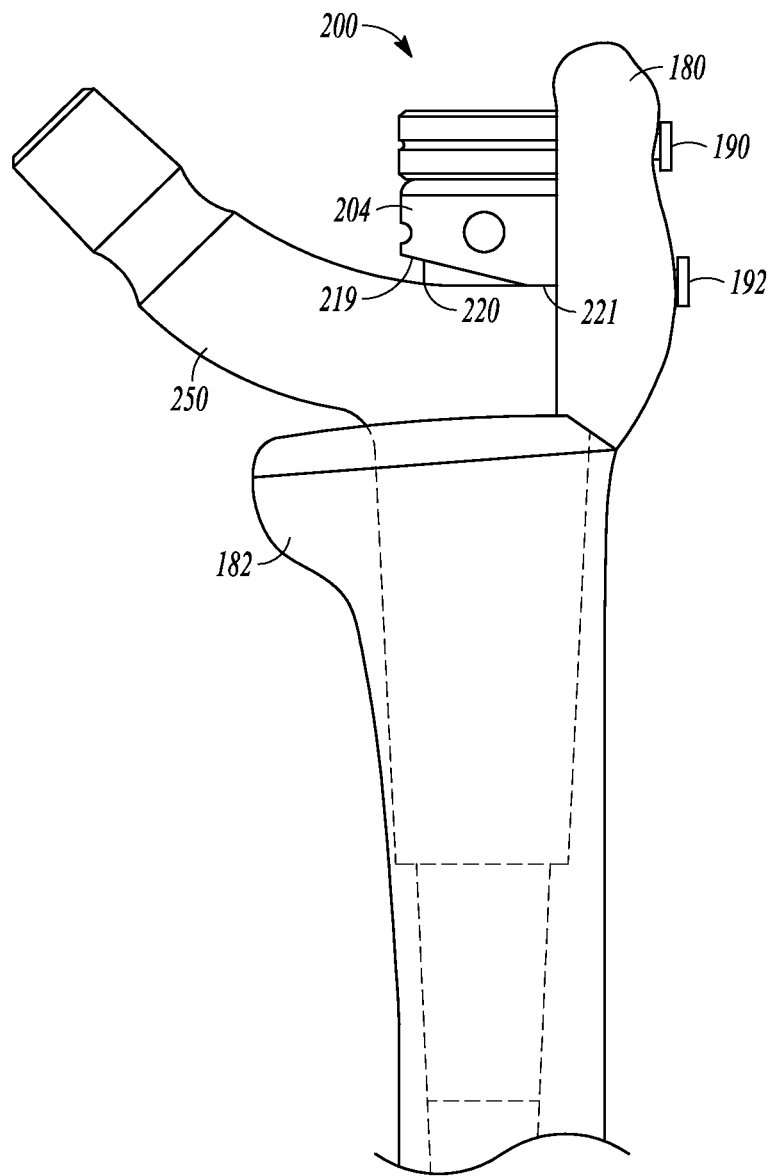
FIG. 9 is a perspective view of the trochanter attachment device of FIG. 7 attached to a hip prosthesis and to a greater trochanter.

FIG. 9 shows an example of the trochanter attachment device 200 attached to a greater trochanter 180, which can be similar to the greater trochanter 16 of FIG. 1. As also shown in FIG. 9, the device 200 can also be implanted in a canal of the femur 182 and attached to a femoral component of a hip prosthesis 250, which can be similar to prosthesis 150 of FIGS. 5 and 6. Fasteners 190 and 192 can extend through the greater trochanter 180, such as to attach the device 200 to the greater trochanter 180, such as also shown in FIG. 10. As visible in FIG. 9, in an example, a second end 220 of the collar 204 can be curved or sloped downward from a front side 219 to a back side 221 of the collar 204. As such, the collar 204 can be configured to engage with a prosthesis having a more angled neck portion compared to the prosthesis shown in FIG. 9. The collar 204 can have more or less of a sloped (or curved) design, if any, from the front 219 to back side 221.

FIG. 10 is a cross-sectional view of what is shown in FIG. 9. Fasteners 190 and 192 can extend through the plate 202 and the insert 209, such as via apertures 210 and 211, respectively, such as to attach the device 200 to the greater trochanter 180. The fasteners 190 and 192 can be drilled or otherwise passed through an outer surface of the greater trochanter 180. The apertures 210 and 211 of the plate 202 and the insert 209 can be preformed with the trochanter attachment device 200. The fasteners 190 and 192, as shown in FIGS. 9 and 10, can be oriented generally perpendicular to the plate 202 and the insert 209; similarly, the apertures 210 and 211 can be oriented generally perpendicular relative to a length of the plate 202 and the insert 209, respectively. In an example, the apertures 210 and 211 can be oriented at an angle relative to the length of the plate 202 and the insert 209, in which case, the fasteners 190 and 192 can be inserted at a corresponding angle.

In an example, the apertures 210 and 211 can be formed as part of the procedure for using the trochanter attachment device 200 to secure the greater trochanter 180 to the femur 182. The user can determine a particular placement and angle of the apertures 210 and 211, which can depend, at least in part, on the particular patient's anatomy and the shape and condition of the patient's greater trochanter.

As shown in FIG. 10 and similarly described above in reference to FIG. 6, the nut 208 of the attachment device 200 can be threaded, such as to engage with both the screw 206 and a stem 258 of the prosthesis 250, each of which can have a threaded outer surface. As also described above in reference to device 200, the nut 208 can include more or less threading. Before or during the procedure to attach the device 200 to the greater trochanter 180, an inner surface of the greater trochanter 180 can be shaped, such as to better engage with the insert 209 and/or the plate 202.

Figure 11:
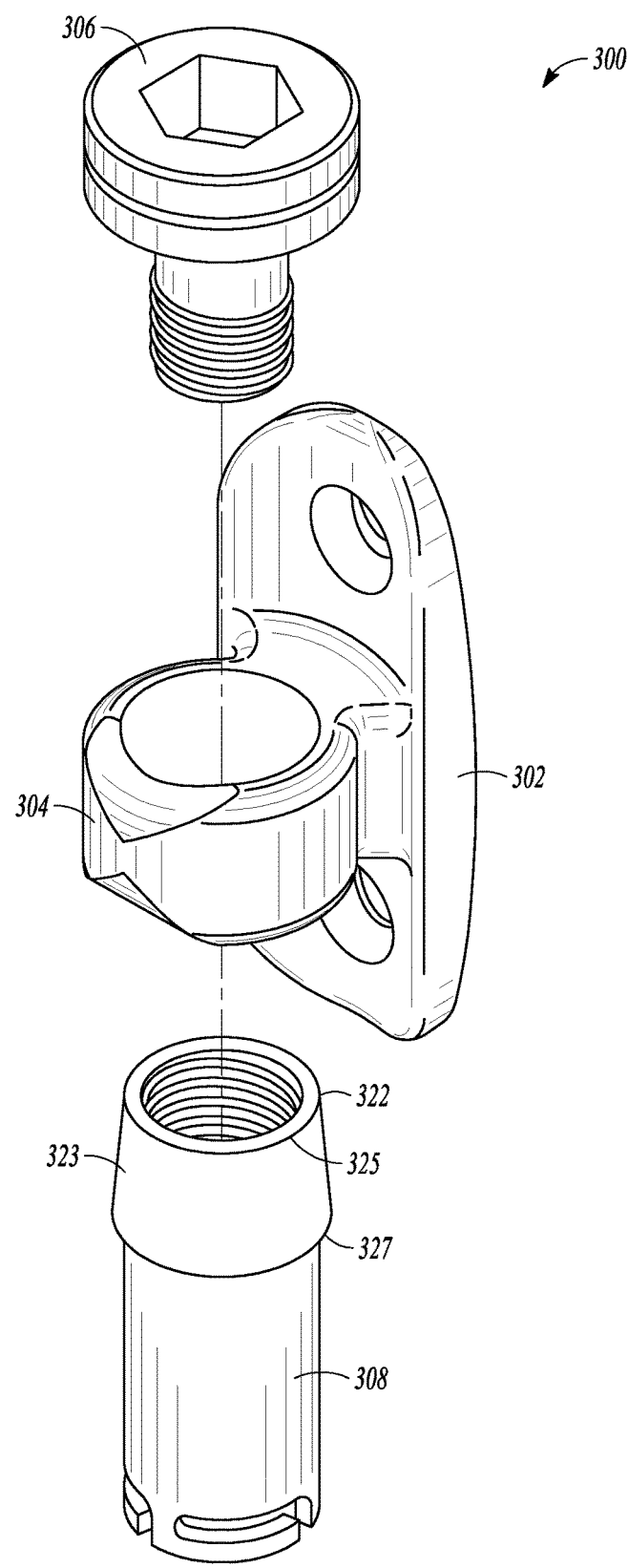
FIG. 11 is an exploded perspective view of an example of a trochanter attachment device in accordance with the present patent application.

FIG. 11 shows an example of a trochanter attachment device 300 similar to the trochanter attachment devices 100 and 200. The trochanter attachment device 300 can include a plate 302, a collar 304, a screw 306, and a nut 308. The trochanter attachment device 300 can include an interference fit between the nut 308 and the collar 304. Such interference fit can include, for example, a taper lock created by the nut 308 and the screw 306. A taper lock can commonly be used for modular connections. The nut 308 can include a cone-shaped portion 323 at or near a first end 322 of the nut 308 and configured to engage with an inside surface of the collar 304. The cone-shaped portion 323 can be shaped or otherwise configured such that the screw 306 can lock the nut 308 into place inside the collar 304. A diameter of the nut 308 at a first end 325 of the cone-shaped portion 323 can be less than a diameter of the nut 308 at a second end 327 of the cone-shaped portion 323. (The first end 325 of the cone-shaped portion 323 can generally coincide with the first end 322 of the nut 308.)

As shown in FIG. 11, in an example, the trochanter attachment device 300 can be configured to not include a ring for attachment to the collar 304 and/or not include an insert for attachment to the plate 302. In an example, the trochanter attachment device 300 can include a ring, like the ring 136 of the trochanter attachment device 100, and/or an insert, like the insert 209 of the trochanter attachment device 200.

The present disclosure includes a method of securing a greater trochanter to the femur, such as using a trochanter attachment device, such as described herein. The method can include attaching a plate of the trochanter attachment device to an inner surface of a greater trochanter, and attaching a collar of the trochanter attachment device to a hip implant implantable in the femur. More specifically, the trochanter attachment device can be attached to the proximal femoral component of a hip implant. The trochanter attachment device can be attached to the hip implant after the hip implant is installed in the diaphysis of the femoral bone. The trochanter attachment device can be attached to the greater trochanter before or after the trochanter attachment device is attached to the hip implant. The method of securing the greater trochanter to the femur can include using at least one reinforcing material or mechanism or device, such as described above, such as to secure the trochanter attachment device to the greater trochanter and the hip implant. Examples of such a reinforcing material, mechanism, or device can include a cable, a wire, a bolt, a suture, or one or more combinations thereof. As described above, the trochanter attachment device can include one or more features that can be sized, shaped, or otherwise configured for receiving or engaging with the reinforcing material, mechanism, or device.

Although specific configurations of a trochanter attachment device are shown in FIGS. 3-11 and particularly described above, other designs of a trochanter attachment device can be used. The trochanter attachment device described herein can be easily configurable, such as for attachment to any of a variety of types of hip implants, including both modular designs, having a detachable stem, and one-piece designs. The trochanter attachment device can also be customized (e.g., provided with at least one patient specific component) such as through the use, for example, of a customizable insert piece, which can be sized, shaped, or otherwise configured to be placed between the plate and the greater trochanter.

In the examples shown in FIGS. 3-11, a screw and a nut can be included, such as for attaching the collar of the trochanter attachment device to the body of the implant, and/or for attaching the device to the stem of the implant. It is recognized that additional or alternative configurations can be used to secure the attachment device to the implant. For example, depending on a length of the screw, a screw of the attachment device can directly attach to the stem of the implant, and as such, a nut may optionally be omitted.

The trochanter attachment device is particularly described herein for use in reattaching the greater trochanter to the femur or reinforcing the existing attachment, or partial attachment, of the greater trochanter to the femur. The trochanter attachment device described herein can also be used in other situations, such as in which the greater trochanter is completely compromised and no longer available for attachment to the femur. In those cases, the plate of the attachment device can be attached to surrounding soft tissue, such as, for example, ligaments and muscles, including the abductor. Particularly if the plate is made of, or coated or otherwise provided with, a porous structure, the attachment device can facilitate soft tissue ingrowth and better stabilize the femoral component of the hip implant to which the attachment device is attached. An attachment device with the insert shown in FIGS. 7-10 can be used to facilitate soft tissue ingrowth, particularly if the insert is made of, or coated or otherwise provided with, a porous structure. An insert made of a porous structure can be used as an alternative to, or in addition to, a plate made of a porous structure.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A trochanter attachment device comprising:
   a plate having an inner surface and an outer surface, the outer surface configured to attach to an inner portion of a greater trochanter of a femur, the inner surface having a top portion, a bottom portion, and a middle portion disposed between the top and bottom portions, and the plate having a longitudinal axis extending from the top portion to the bottom portion; and
   a collar connected to and extending from the middle portion of the inner surface of the plate, the bottom portion of the plate extending past a bottom end of the collar, the collar having an aperture configured to receive a collar fastener to attach the trochanter attachment device to a hip implant having a neck, the aperture extending through the collar in a direction generally parallel to the longitudinal axis of the plate, wherein the plate and collar are separate components from the hip implant, and the bottom end of the collar is configured to contact a top surface of the neck of the hip implant, when the trochanter attachment device is attached to the hip implant.

2. The trochanter attachment device of claim 1, wherein the plate includes an aperture for receiving a plate fastener to attach the plate to the greater trochanter.

3. The trochanter attachment device of claim 2, wherein the aperture of the plate extends from the inner surface to the outer surface of the plate.

4. The trochanter attachment device of claim 3, wherein the plate fastener is configured to extend through an outer surface of the greater trochanter and through the aperture of the plate.

5. The trochanter attachment device of claim 1, wherein the collar is oriented generally perpendicular to the plate such that, when the collar fastener is received through the aperture in the collar, the collar fastener and the plate extend in a direction generally parallel to each other.

6. The trochanter attachment device of claim 1, wherein the collar fastener comprises a screw and a nut, and wherein the nut is configured to engage with the screw and a stem of the hip implant.

7. The trochanter attachment device of claim 6, wherein the nut comprises:
   a first end portion, having a threaded portion configured to engage with the screw; and
   a second end portion, having a threaded portion configured to engage with the stem of the hip implant.

8. The trochanter attachment device of claim 6, wherein the nut comprises a spline on an outer surface of the nut, and wherein the spline is configured to engage with an inside surface of the collar.

9. The trochanter attachment device of claim 6, wherein a first end portion of the nut includes a cone-shaped portion configured to engage with an inside surface of the collar.

10. The trochanter attachment device of claim 1, wherein when the trochanter attachment device is attached to the hip implant, the top portion of the plate is configured to extend above the top surface of the neck of the hip implant, and the bottom portion of the plate is configured to extend below the top surface of the neck of the hip implant.

11. The trochanter attachment device of claim 1, further comprising:
   an insert, configured to be attachable to the outer surface of the plate, and configured to attach the plate to the greater trochanter, and the insert includes a porous portion.

12. A trochanter attachment device for use with a hip implant having a neck portion and a stem portion, the trochanter attachment device comprising:
   a plate having an inner surface, an outer surface, a proximal end and a distal end, the outer surface configured to attach to an inner portion of a greater trochanter of a femur, the plate having one or more apertures for receiving one or more plate fasteners to attach the plate to the greater trochanter, and the plate having a longitudinal axis extending from the proximal end to the distal end; and
   a collar connected to and extending from the inner surface of the plate, the collar having a top and a bottom, the bottom configured to contact a top surface of the neck portion of the hip implant, the collar having an aperture configured to receive a collar fastener to attach the trochanter attachment device to the hip implant, the aperture extending through the collar in a direction generally parallel to the longitudinal axis of the plate, wherein the plate and the collar are a singular piece and include a porous tantalum region.

13. The trochanter attachment device of claim 12, wherein the collar fastener comprises:
   a screw, configured to extend through the collar for securing the collar to the hip implant; and
   a nut, having a first end portion and a second end portion, wherein the first end portion is configured to engage with the collar and the screw, and the second end portion is configured to engage with a stem portion of the hip implant.

14. The trochanter attachment device of claim 12, further comprising a ring including a groove extending at least partially circumferentially around an outer surface of the ring, wherein the ring is configured to be attachable to an outer surface of the collar.

15. The trochanter attachment device of claim 12, the collar includes a groove on an outer surface of the collar, configured for receiving a reinforcing material.

16. The trochanter attachment device of claim 12, wherein the one or more apertures of the plate extend from the inner surface to the outer surface of the plate.

17. The trochanter attachment device of claim 16, wherein the one or more plate fasteners are configured to extend through an outer portion of the greater trochanter and through the one or more apertures of the plate.

18. A trochanter attachment device comprising:
   a plate having an inner surface and an outer surface;
   a collar connected to the inner surface of the plate and having an aperture configured to receive a collar fastener to attach the trochanter attachment device to a hip implant; and
   a plate insert separate from the plate and collar in a disassembled position of the trochanter attachment device, the plate insert including a porous portion, wherein when the trochanter attachment device is in an assembled/implanted position, the plate insert is attached to the outer surface of the plate to secure the plate to an inner portion of a greater trochanter of a femur.

* * * * *